United States Patent
Brocardo et al.

(10) Patent No.: US 9,782,519 B2
(45) Date of Patent: Oct. 10, 2017

(54) ULTRASOUND COUPLING LIQUID AND CONTAINER

(71) Applicant: THERACLION SA, Malakoff (FR)

(72) Inventors: Roberta Brocardo, Paris (FR); Thierry Pechoux, Paris (FR)

(73) Assignee: Theraclion SA, Malakoff (FR)

( * ) Notice: Subject to any disclaimer, the term of this patent is extended or adjusted under 35 U.S.C. 154(b) by 0 days.

(21) Appl. No.: 14/979,883

(22) Filed: Dec. 28, 2015

(65) Prior Publication Data

US 2016/0199026 A1 Jul. 14, 2016

Related U.S. Application Data

(62) Division of application No. 13/643,151, filed as application No. PCT/EP2011/057868 on May 16, 2011, now Pat. No. 9,220,659.

(30) Foreign Application Priority Data

May 25, 2010 (EP) ..................................... 10163725

(51) Int. Cl.
| | | |
|---|---|---|
| A61B 8/00 | (2006.01) | |
| A61L 31/04 | (2006.01) | |
| A61N 7/02 | (2006.01) | |
| A61J 1/00 | (2006.01) | |
| A61J 1/14 | (2006.01) | |
| B65D 1/00 | (2006.01) | |

(52) U.S. Cl.
CPC ............. A61L 31/048 (2013.01); A61N 7/02 (2013.01); A61B 8/4281 (2013.01); A61B 8/546 (2013.01); A61J 1/00 (2013.01); A61J 1/1475 (2013.01); B65D 1/00 (2013.01)

(58) Field of Classification Search
None
See application file for complete search history.

(56) References Cited

U.S. PATENT DOCUMENTS 4,641,362 A    2/1987  Muller
4,886,068 A *  12/1989 Kaneko ................ A61B 8/4281
                                          600/437

(Continued)

FOREIGN PATENT DOCUMENTS

JP    S5944247 A    3/1984
JP    2092343 A     4/1990

(Continued)

OTHER PUBLICATIONS

English language translation of the foreign reference, JPS5944247A, (JP S5944247A is dated Mar. 12, 1984).*

(Continued)

Primary Examiner — Bethany Barham
Assistant Examiner — Dominic Lazaro
(74) Attorney, Agent, or Firm — Davis & Bujold PLLC; Michael J. Bujold

(57) ABSTRACT

A coupling liquid for ultrasound devices, preferably high intensity focused ultrasound (HIFU). The coupling liquid comprises a liquid aqueous solution of at least one hydrophilic polymer having an average molecular mass of between 30,000 and 70,000 and at least one alcohol with a carbon chain of 1 to 7 carbon atoms. Also disclosed is a container (10) for an ultrasound coupling liquid having a thin wall.

2 Claims, 4 Drawing Sheets

(56) References Cited

U.S. PATENT DOCUMENTS

Figure 1:
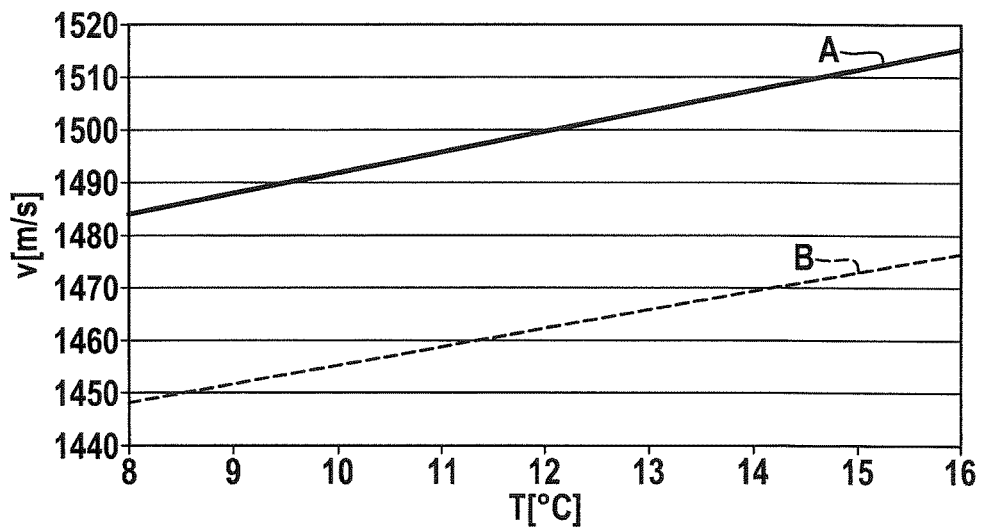

| | | | |
|---|---|---|---|
| 5,023,119 | A | 6/1991 | Yamakoshi |
| 5,078,149 | A | 1/1992 | Katsumata et al. |
| 6,126,619 | A | 10/2000 | Peterson et al. |
| 6,432,069 | B1 * | 8/2002 | Godo .................. A61B 8/4281 600/439 |
| 6,626,855 | B1 | 9/2003 | Weng et al. |
| 7,559,905 | B2 | 7/2009 | Kagosaki et al. |
| 8,721,553 | B2 | 5/2014 | Lee et al. |
| 2008/0051937 | A1 | 2/2008 | Khan et al. |
| 2009/0030396 | A1 | 1/2009 | Ferris |
| 2009/0112098 | A1 | 4/2009 | Vaezy et al. |
| 2010/0032450 | A1 | 2/2010 | Ahlund et al. |

FOREIGN PATENT DOCUMENTS

| | | | |
|---|---|---|---|
| JP | 2000-316871 | A1 | 11/2000 |
| JP | 2003038485 | A | 2/2003 |
| JP | 2009-000513 | A | 1/2009 |
| JP | 2010504172 | A | 2/2010 |
| WO | 2006/032059 | A2 | 3/2006 |
| WO | 2008/137944 | A1 | 11/2008 |
| WO | 2010/016789 | A1 | 2/2010 |

OTHER PUBLICATIONS

English Abstract of Japanese Pre-Trial Reexamination Report issued in corresponding Japanese Patent Application No. 2013-511605 dated Feb. 5, 2016.
Translation of the Japanese Office Action issued in the corresponding Japanese Patent Application No. 2013-511605 mailed Feb. 28, 2017.
Japanese Office Action issued in corresponding Japanese Patent Application No. 2015-22764 dated Feb. 21, 2017.

* cited by examiner

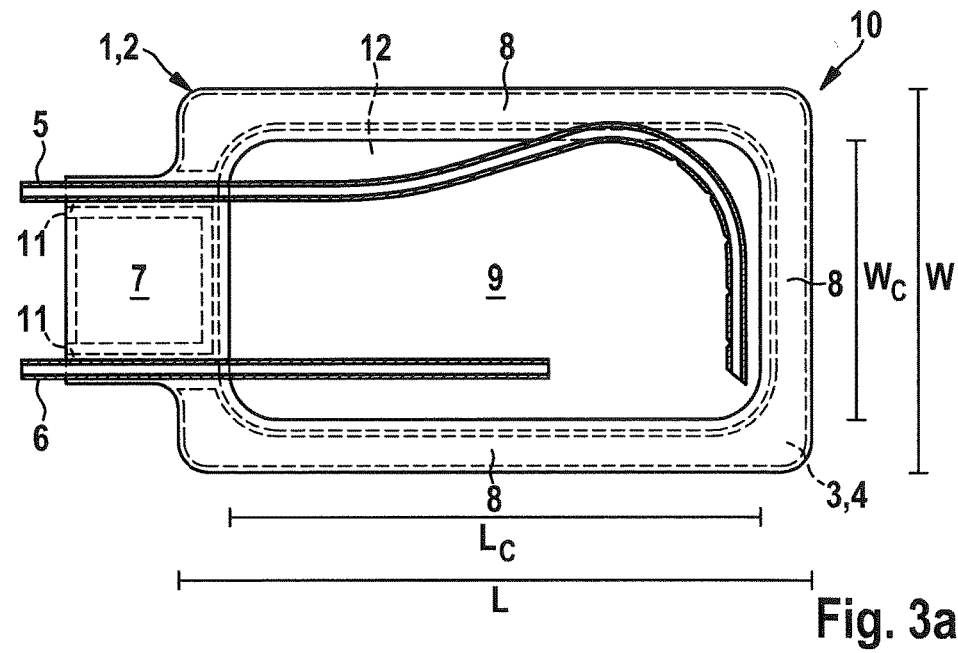
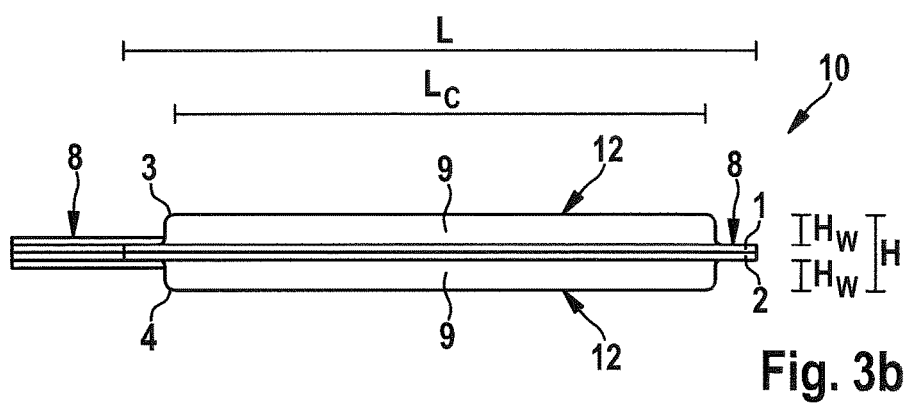
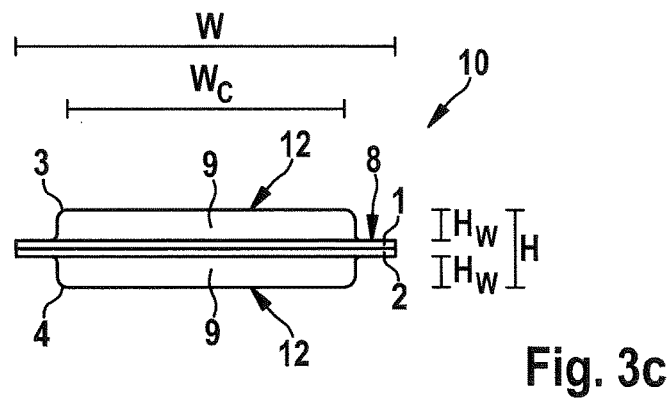

ULTRASOUND COUPLING LIQUID AND CONTAINER

This invention relates to a coupling liquid for ultrasound imaging or treatment as well as to a container filled with a coupling liquid.

The use of ultrasound is known for imaging purposes. But ultrasound may also be used for therapeutic purposes, either for the destruction of concretions by mechanical effect or in order to create lesions in tissue by thermal effect.

In both cases, use of a coupling liquid between the ultrasound transducer and the skin of the patient is advantageous. The coupling liquid ensures proper transmission of ultrasound waves from the ultrasound transducer to the skin. The coupling liquid may be applied directly on the skin, thus forming a bridging layer between the skin and the ultrasound transducer. Such a direct application is mostly used with imaging transducers. Alternatively, the coupling liquid may be contained in a balloon-like cover member affixed on an ultrasound transducer. Such a configuration is mostly used with high intensity focused ultrasound (HIFU) transducers, where the coupling liquid additionally serves as cooling liquid to both cool the transducer and the skin. The coupling liquid is advantageously being constantly cycled through additional cooling means, such as a heat exchanger.

Known coupling liquids are mostly water based hydrogels. Known gelling agents are mostly polymers, for example polyurethanes, polyols and the like.

One major problem with coupling liquids is that when high ultrasound energies are used, e.g. in a HIFU treatment, bubbles are formed in the liquid by a cavitation effect. Such bubbles may cause problems when additional ultrasound imaging is used to monitor the treatment and/or to position the focal point of the ultrasound waves.

Japanese patent application 2 92343 discloses a coupling product for ultrasound imaging formed by a matrix of porous material like polyurethane which contains an aqueous gel such as polyvinylpyrrolidone.

U.S. Pat. No. 5,078,149 describes an ultrasound coupling product having a recipient containing a polymer gel. The recipient may be attached to the tip of an ultrasound probe to serve as coupling member. The polymer is integrally crosslinked with the recipient.

Such coupling products have the disadvantage that they are not pumpable and thus may not provide any cooling to the ultrasound transducer or the skin.

U.S. Pat. No. 6,432,069 discloses an aqueous coupling liquid comprising a hydrophilic polymer, preferably polyvinylpyrrolidone. The polymer is present in an amount of between 10 and 50 g/L. The liquid is specifically optimized for the use in high energy ultrasound applications, like HIFU treatment, since almost no bubbles are formed due to the cavitation effect. Moreover, as the viscosity of the liquid is below $2 \cdot 10^{-4}$ Pa·s it is readily pumpable and may thus also act as cooling liquid. For this purpose, the coupling liquid is constantly pumped through a cover member covering an ultrasound transducer.

However, at the boundary between the coupling liquid and the cover member and/or skin of the patient, a certain amount of ultrasound waves are reflected due to the different refraction indexes of the materials. Moreover, as some of the used polymers are of organic nature, bacterial and algal growth might occur, thus making a sterilization of the liquid necessary.

It is an objective of the present invention to overcome the disadvantages of the known coupling liquids and especially to provide an ultrasound coupling liquid leading to less reflexion of the ultrasound waves and which is not prone to bacterial or algal growth. This problem is solved with a coupling liquid according to claim 1.

The ultrasound coupling liquid of the present invention comprises:

a. a liquid aqueous solution of at least one hydrophilic polymer having an average molecular mass of between 30,000 and 75,000
b. at least one alcohol with a carbon chain of 1 to 7 carbon atoms A "hydrophilic polymer" as understood herein means a polymer which has a sufficient affinity to water as to dissolve therein or to form a gel with it. Suitable examples of hydrophilic polymers are: acrylic polymers, poly(vinyl alcohol), cellulose derivatives, gelatine, gums such as e.g. guar or agaragar, poly(ethylene oxide), polyvinylpyrrolidone or mixtures thereof.

Preferably, the coupling liquid comprises a single hydrophilic polymer. Polymers with an average molecular mass in the range of between 30,000 and 70,000 present at a low concentration, such as between 10 and 50 g/L allow the production of hydrogels having a relatively low viscosity, preferably between $1 \cdot 10^{-4}$ Pa·s and $2 \cdot 10^{-4}$ Pa·s at 20° C. Such a viscosity allows the hydrogel to be readily pumped and thus used in a liquid circuit with a cooling unit.

Further, the coupling liquid comprises at least one alcohol with a carbon chain of 1 to 7 carbon atoms. The carbon chain may be branched or unbranched. Preferably the alcohol is selected from ethanol, butanol, propanol, isopropanol, pentanol, hexanol, heptanol or mixtures thereof. More preferably, the at least one alcohol is a primary alcohol.

Surprisingly, addition of an alcohol to a coupling liquid comprising a hydrophilic polymer was found to considerably reduce the reflection of ultrasound waves at the boundary between the coupling liquid and the skin and/or a cover member covering an ultrasound transducer. Moreover, reduction of the refractive index between the coupling liquid and the skin and/or the cover member shifts the focal point of the ultrasound waves deeper into the body. An additional effect is that bacterial and/or algal growth is hindered by the alcohol. Another additional effect is that the freezing point of the coolant is lowered with the addition of alcohol. Whereas the low temperature of known cooling fluids is limited to 0° C., the coolant according to the invention can be cooled to less than 0° C. yielding a potentially better efficiency. For example adding 5.5% ethanol lowers the freezing point to −2° C.

The at least one alcohol is preferably present in a concentration of 3 to 45% by weight of the total weight of the coupling liquid, preferably 5 to 20%. The amount of ultrasound wave reflections is reduced when the alcohol concentration is in this range.

Most preferably the at least one alcohol is present in a concentration of 5% by weight of the total weight of the coupling liquid. This concentration was found to be the optimal concentration for a coupling fluid used with high energy ultrasound, especially with HIFU treatment.

The at least one alcohol is preferably selected from a group comprising of ethanol, propanol, isopropanol and/or benzyl alcohol. These alcohols have good antibacterial and antifungal properties. Thus, the coupling liquid does not need to be sterilized before packaging or use.

The hydrophilic polymer preferably is or comprises polyvinylpyrrolidone. Polyvinylpyrrolidone has about the same acoustic and absorption characteristics as water, thereby allowing the use of varying concentrations of polyvinylpyrrolidone with only minor changes in the overall characteristics of the solution.

These low attenuation and/or acoustic absorption characteristics of the coupling liquid ensure that a major portion of the ultrasound waves are effectively transmitted towards the skin rather than being absorbed by the coupling liquid.

The polyvinylpyrrolidone used in the present invention most preferably has an average molecular mass of 58,000, like e.g. polyvinylpyrrolidone available under the trademark Plasdone® K-29/32 (ISC Corp., USA).

Most preferably, the hydrophilic polymer is present in an amount of between 1% and 5% weight/volume of the coupling liquid. This allows obtaining a hydrogel with a viscosity which is sufficiently low to render the gel pumpable. The viscosity of the coupling liquid according to the present invention preferably is between $1 \cdot 10^{-4}$ Pa·s and $2 \cdot 10^{-4}$ Pa·s at 20° C., more preferably between $1.2 \cdot 10^{-4}$ Pa·s and $1.6 \cdot 10^{-4}$ Pa·s at 20° C.

Another objective of the present invention is to provide a container for a coupling fluid which is easy to integrate in a cooling system of an ultrasound device and which is protected from bacterial and fungal growth. This problem is solved by a container as described below.

The container according to the present invention has an outer wall with a high thermal conductivity defining a cavity filled with an ultrasound coupling liquid comprising a preservative. The ultrasound coupling liquid preferably is a coupling liquid according to the present invention.

As "high thermal conductivity" as understood herein is a heat conductivity of more than 1000 W/K per m² of wall surface. This allows for a good heat transfer from the container to the cooling system, thereby allowing efficient temperature reduction in the coolant.

The wall preferably has a tensile strength of more than 30 N/mm². This avoids rupture of the container wall during handling, storage and/or transportation.

A container with a thin wall may not be sterilized by heat since the wall would not be able to withstand the internal pressure changes caused by the expansion of the liquid enclosed, and thus would be prone to bursting. A thin wall container may also be more prone to deformation due to softening of the wall material when heated. Sterilizing methods other than heat, such as gamma exposure or ethylene oxide (ETO) gas are also prone to modifying the material of the container walls or of the coupling liquid itself. The presence of a preservative in the coupling liquid eliminates the sterilization step, since growth of bacteria or fungi will be hindered. This allows the production of coupling liquid containers under non-sterile conditions, thereby lowering the production costs quite considerably.

For ease of use of an ultrasound device, especially in the field of HIFU treatment, it is important that the coupling liquid may be easily introduced into a liquid cooling cycle. By providing a container with a wall with a high thermal conductivity according to the present invention, it is possible to place the container onto or into cooling means, such as between two cooling plates or into a cooling bath. A high heat conductivity of the wall thus allows an effective heat transfer between the coupling liquid within the container and the cooling means. Hence, it is not necessary to remove the coupling liquid from the container and to fill it into a cooling system.

The preservative comprised in the coupling fluid filled in the container according to the present invention may be any suitable preservative hindering the growth of microorganisms, especially bacteria and fungi, as long as the acoustic properties are preserved or improved. Preferably the preservative comprised in the coupling liquid is an alcohol. Most preferably, the coupling liquid is a coupling liquid as described in the present invention comprising a hydrophilic polymer and an alcohol having a branched or unbranched carbon chain with 1 to 7 carbon atoms.

Preferably, the wall has a thickness of less than 0.5 mm, more preferably less than 0.25 mm, most preferably less than 0.125 mm. Reducing the thickness of the wall will increase the thermal conductivity across the wall and hence the heat exchange between the coupling liquid inside the container and a cooling means. Reduction of the thickness of the wall the values indicated above even allows the wall to comprise or be made of a material which has a low thermal conductivity.

Reducing the thickness of the wall will also render it more flexible thus allowing for a quicker and better distribution of any pressure peak applied on the wall. This reduces the risk that the wall is locally ripped apart by such a pressure peak.

The wall preferably is made of or comprises a polymeric material.

Polymeric materials are readily available and cheap. Furthermore, there are many techniques known in the art to impart a specific shape to a polymeric material, like injection moulding, extruding, punching as well as vacuum or heat forming. This greatly facilitates the production process of a container according to the present invention.

Most preferably, the thin wall is made of or comprises poly(vinyl chloride). Use of poly(vinyl chloride) allows the manufacture of containers having very thin walls. Moreover, poly(vinyl chloride) can be handled easily and does not require special disposal after use.

Preferably, the container additionally comprises means to bring the cavity in fluid connection with an ultrasound probe head. Said means preferably comprise at least one tube. By the connection means, it is possible to integrate the container into a liquid circuit of an ultrasound device. For example, the coupling liquid may be constantly cycled by means of a pump from the container to the ultrasound probe head. Since the container has a thin outer wall, it may be placed on or inside a cooling means, such that the coupling liquid may additionally serve as cooling liquid.

Additionally, the container most preferably is airtight. By airtight is understood that no gas exchange between the cavity of the container and the atmosphere outside of the container is possible. This additionally reduces the probability of contamination of the coupling liquid with any microorganisms. Of course, once the container is connected with an ultrasound device or is opened for the withdrawal of liquid, it may no longer be airtight. Preferably, connection of the container with an ultrasound device is configured in such a way as to keep the entire liquid circuit airtight.

The container preferably comprises at least one frame element defining the geometrical shape of the container in one plane and two wall elements, wherein said two wall elements are fixed over said frame element thereby forming the cavity in between said two wall elements.

The frame element preferably is of rectangular shape. But the frame member may also be of any other suitable shape, such as circular. The frame element may also comprise additional elements, such as protrusions and/or recesses for additional functions, such as handholds and/or fixation means. The frame element preferably is more rigid than the outer walls, thus imparting some stability to the container in the plane of the frame element. Two wall elements are fixed over the frame element, one on either side of the frame element. Between the wall elements, the cavity is thus formed. The wall elements may be fixed to the frame element by gluing or welding, Alternatively the container may comprise more than one frame element, such as two, three or more frame elements. Preferably, if the container comprises more than one frame element, the frame elements are fixed one above the other, e.g. by welding or gluing. This additionally reinforces the stability of the container in the plane of the frame elements.

The frame elements preferably comprise or are made of the same material as the wall elements. Alternatively, the frame elements may comprise or be made of another material as the wall elements.

The container preferably additionally comprises an identification means, preferably an RFID tag. The identification means may enable to retrieve information about the coupling liquid in the container, such as e.g. batch serial number, production date, kit serial number or even last date of use.

Another objective of the present invention is to provide a method of use of an ultrasound device with improved acoustic qualities.

In the method of use of an ultrasound device, preferably a HIFU device, a container filled with a coupling liquid comprising a preservative, preferably according to the present invention, is brought in fluid connection with the ultrasound transducer.

The container may be brought in fluid connection via connection means, preferably comprised with the container. Preferably the container is brought in fluid connection with the ultrasound device by means of at least one tube, preferably a flexible tube.

This invention further relates to the use of a coupling liquid of the present invention for a treatment with ultrasound, preferably with high intensity focused ultrasound.

Another object of the present invention is to provide an ultrasound device comprising fixation means to reversibly connect a container of the present invention to the ultrasound device. The fixation means most preferably are in the form of an adaptor member which is configured to reversibly house a container. Most preferably, the adaptor member is a separate device of the ultrasound device, which is insertable in a receptacle provided on the ultrasound device. Alternatively, the adaptor device may also be provided as unitary part of the ultrasound device.

Most preferably, the container filled with a coupling liquid is a container according to the present invention.

Additional aspects and details of the present invention will be apparent from the following description of figures and examples.

Figure 2:
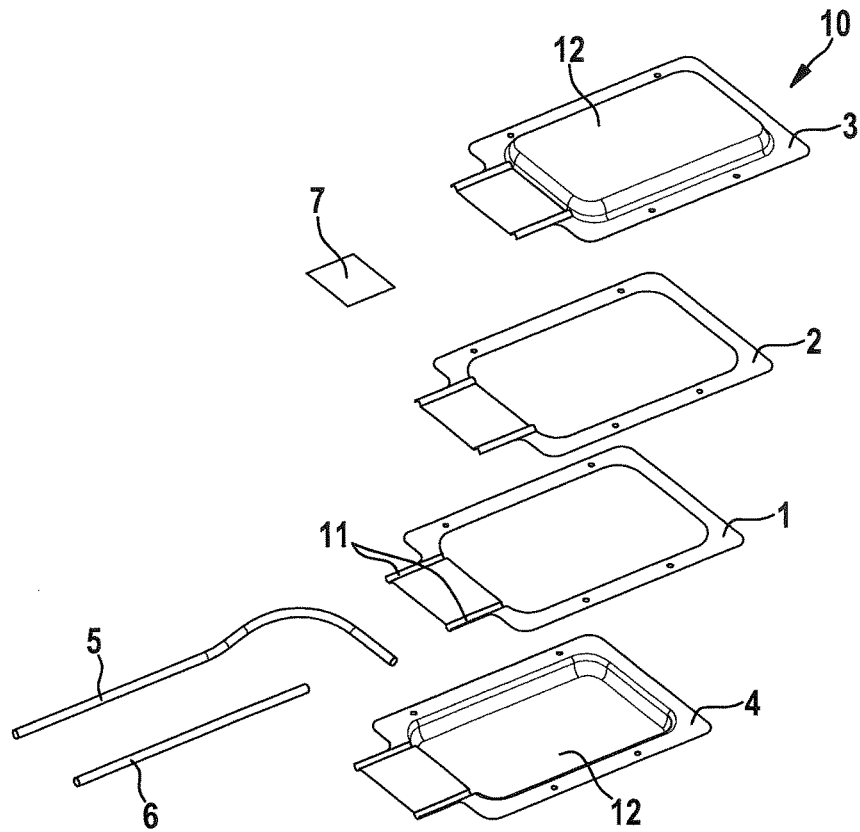
Figure 4:
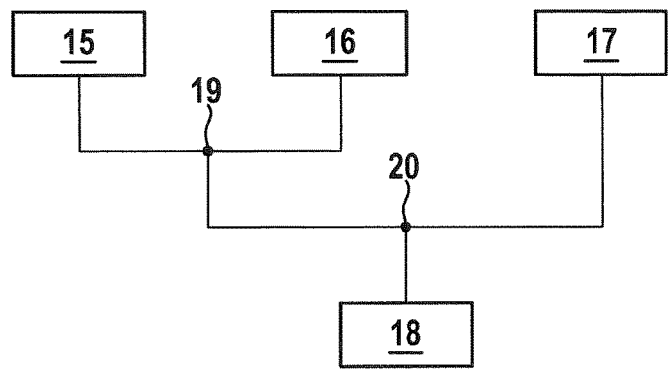
Figure 5A:
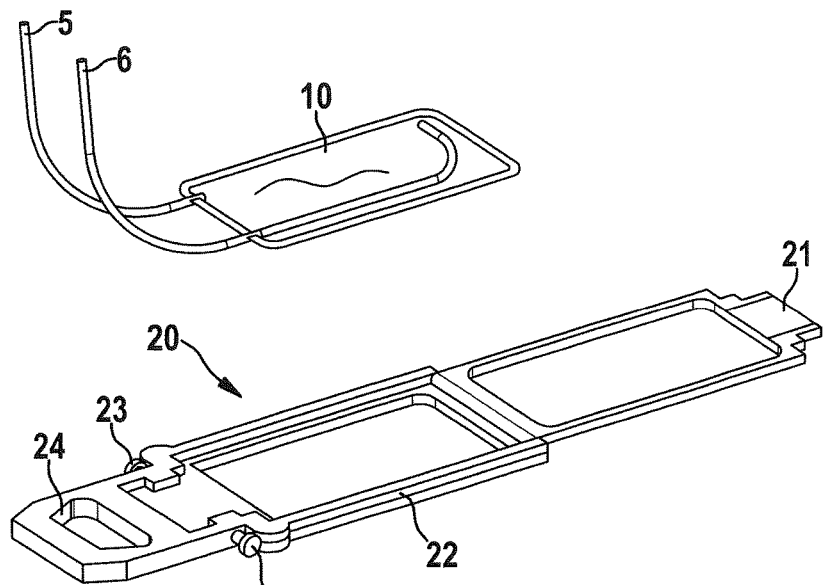
Figure 5B:
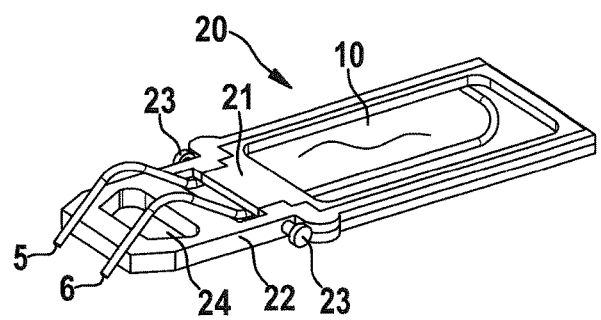
Figure 6:
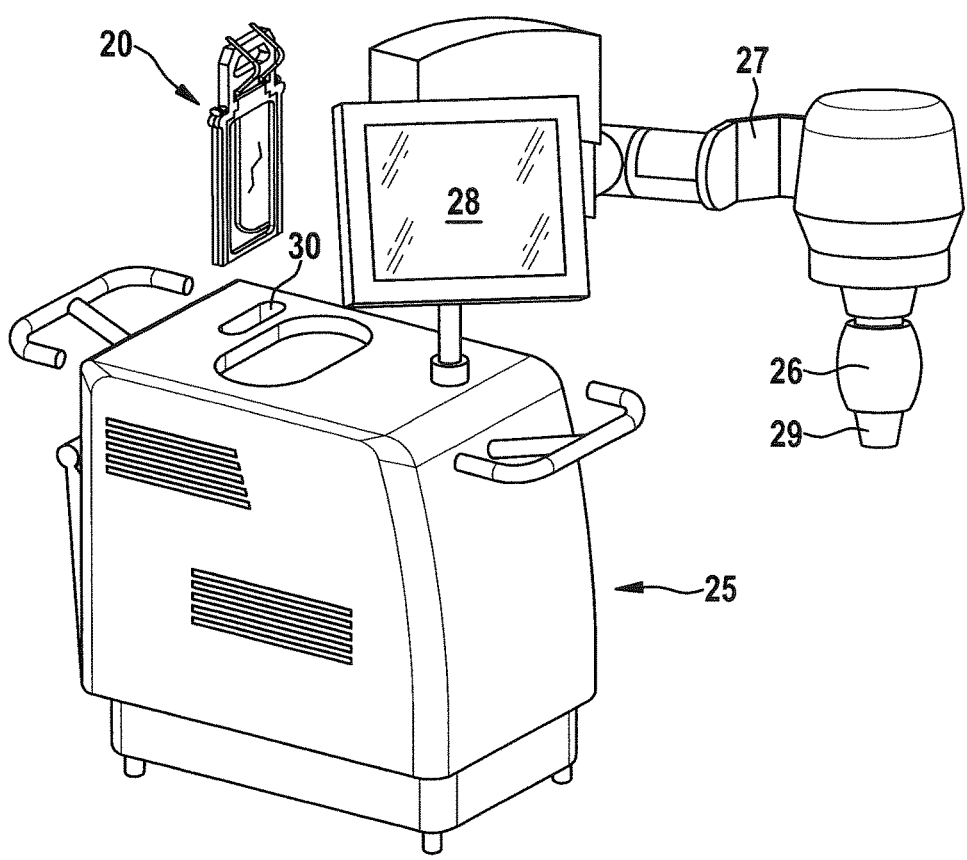

FIG. 1: Diagram showing the difference in speed of sound in a coupling liquid with alcohol compared to a coupling liquid without alcohol;

FIG. 2: An exploded view of an embodiment of a coupling liquid container according to the present invention;

FIGS. 3a, 3b and 3c: The coupling liquid container of FIG. 2 viewed from different sides;

FIG. 4: Schematic representation of a preferred method of manufacturing of a coupling liquid according to the present invention;

FIGS. 5a and 5b: Fixation means for fixing a container of the present invention to an ultrasound device;

FIG. 6: An ultrasound device comprising connection and cooling means for a container according to the present invention.

FIG. 1 shows the difference in the speed of sound at various temperatures between a coupling liquid comprising 10% w/v of polyvinylpyrrolidone in water, shown as line B, compared to a coupling liquid additionally comprising 5% by weight of ethanol, shown as line A. As can readily be seen, the addition of alcohol increases the speed of sound in the coupling medium.

Additionally, the reflection coefficient of the ultrasound waves between the liquid and the skin or cover member decreases, thus allowing increased transmission of the sound waves from the liquid into the tissues of a patient. Exemplary values for different physical characteristics of a coupling liquid of the present invention compared to a coupling liquid without alcohol and with plain water are shown in table 1:

TABLE 1

|  | Water | Coupling liquid | Coupling liquid with 5% ethanol |
|---|---|---|---|
| Density ρ [g/cm3] | 1 | 1.006 | 0.9935 |
| Impedance Z [MRay] | 1,457 | 1,465 | 1,482 |
| Reflection coefficient R of sound on cover member made of silicon | $12 * 10^{-4}$ | $9.85 * 10^{-4}$ | $6.64 * 10^{-4}$ |

The development of bacterial contamination was tested both for a coupling medium comprising 10% weight by volume polyvinylpyrrolidone in water as well as a coupling liquid additionally comprising 5% by weight of ethanol. Further, a coupling liquid comprising alcohol was inoculated with a bacterial culture of *Pseudomonas aeruginosa* at 80 CFU/100 mL. The coupling liquid probes were filled in a pouch container excluding any air and the pouches were stored for 5 months at room temperature. Samples of the liquid were taken and incubated for 3 days at 22° C.±2° C. After this time, bacterial contamination was determined. The results are shown on table 2:

TABLE 2

| Container | Ethanol | Innoculation | Contamination after 1.5 mts | Contamination after 5 mts |
|---|---|---|---|---|
| 1 | — | — | overgrown | 500000 UFC/mL |
| 2 | — | — | overgrown | 740000 UFC/mL |
| 3 | — | — | overgrown | 570000 UFC/mL |
| A | 5% | — | 1 CFU/100 mL | 0 CFU/100 mL |
| B | 5% | — | 0 CFU/100 mL | 0 CFU/100 mL |
| C | 5% | — | 0 CFU/100 mL | 0 CFU/100 mL |
| D | 5% | 80 CFU/100 mL | 34 CFU/100 mL | 0 CFU/100 mL |
| E | 5% | 80 CFU/100 mL | 40 CFU/100 mL | 0 CFU/100 mL |
| F | 5% | 80 CFU/100 mL | 58 CFU/100 mL | 0 CFU/100 mL |

As can be seen, addition of an alcohol with a carbon chain of 1 to 7 carbon atoms, in this case ethanol, hinders bacterial growth in a coupling liquid. Even if the coupling liquid was not manufactured under aseptic conditions and therefore contains low levels of bacterial contamination, overgrowing of the liquid by bacteria can be avoided by addition of ethanol.

In a test, the focal point of an imaging transducer was shifted from 11 mm to 13.7 mm from the tip of the probe using a coupling liquid with 5% ethanol.

FIG. 2 shows an exemplary embodiment of a container of the present invention in exploded view. The container 10 comprises a first frame element 1 and a second frame element 2. In this embodiment, the frame elements 1,2 are generally of rectangular shape. On both sides of the frame elements 1,2 two wall elements 3,4 are affixed. Preferably, the frame elements 1,2 provide passages 11 for the insertion of tubes 5,6 into the cavity formed between the two walls 3,4. Identification means 7, exemplarily shown as RFID chip, may be inserted between the two frame elements 1,2. Between the walls 12 a cavity is formed.

FIG. 3a shows a top view of an assembled container 10. Both wall elements 3,4 are fixed on the frame elements 1,2. This creates a border 8 at the edges of the wall elements 3,4. Wall elements 3,4 may be affixed to frame elements 1,2 by means of gluing or plastic welding. Frame elements 1,2 are also fixed together by means of gluing or plastic welding. Between the wall elements 3,4 cavity 9 is formed. Tubes 5,6 are inserted into cavity 9 through passages 11. By means of the tubes 5,6 the container 10 may be connected to an ultrasound device or to a liquid circuit of an ultrasound device.

FIGS. 3b and 3c are side and front views, respectively, of the assembled container 10 as shown on FIG. 3a. Both wall elements 3,4 have a height $H_w$. The overall height H of the container 10 is the sum of the height $H_w$ of the two wall elements 3,4 and the thickness of both frame elements 1,2. The height $H_w$ of the wall elements 3,4 is a maximal height. If the walls 12 are flexible and the cavity 9 is not completely filled, then the walls 12 may not extend to their full height $H_w$.

Both the frame elements 1,2 and the wall elements 3,4 are made of a polymeric material, preferably poly(vinyl chloride). Alternative embodiments may also provide for a container where the frame elements 1,2 comprise or are made of another material than the wall elements 3,4.

The thickness of the wall elements 3,4 and hence of the walls 12 preferably is 0.1 mm. The frame elements 1,2 are preferably thicker than the wall elements 3,4. Preferably, thickness of the frame elements 1,2 is between 0.1 mm an 1.5 mm, more preferably between 0.2 mm and 1 mm. Most preferably, the frame elements 1,2 are 0.25 mm thick.

The cavity 9 preferably has a with $W_c$ in the range of 90 mm to 150 mm, more preferably of 100 mm to 125 mm. Most preferably width $W_c$ is 110 mm. The length $L_c$ of cavity 9 is in the range of 180 mm to 250 mm, more preferably of 200 mm to 225 mm. Most preferably, the length $L_c$ is 210 mm.

The with of the container W is preferably in the range of 120 mm to 180 mm, more preferably of 140 mm to 160 mm. Most preferably width W is 150 mm. The length of the container L preferably is in the range of 250 mm to 350 mm, more preferably of 280 mm to 320 mm. Most preferably, length L is 295 mm.

Height $H_w$ of the wall elements 3,4 preferably is in the range of 5 mm to 20 mm, more preferably of between 10 mm to 15 mm, most preferably height $H_w$ is 12 mm.

The height $H_w$ of the container 10 when filled is preferably in the range of 12 mm to 50 mm, more preferably of between 20 mm and 35 mm, most preferably the height H of container 10 is 22 mm.

The total volume of the cavity 9 of container 10 most preferably is 500 mL.

FIG. 4 shows a preferred method of manufacturing of a coupling liquid according to the present invention. In a first mixing step 19, an alcohol 15 is added to a powder of a hydrophilic polymer 16. Preferably, alcohol 15 is ethanol and polymer 16 is polyvinylpyrrolidone. The amount used may vary depending on the wanted characteristics of the coupling liquid. Preferably, 10 grams of a polyvinylpyrrolidone, preferably with an average molecular weight of about 58,000, e.g. as available under the name PLASDONE K29-32 (ISP Corp.), are dissolved in 50 grams of ethanol in the first mixing step 19. This solution is then mixed with water, preferably purified or distilled water in a second mixing step 20. The amount of water should be chosen such as to yield 1 liter of coupling liquid 18. Alternatively, additional compounds may be added to the coupling liquid 18 during any of the manufacturing steps, e.g. in first mixing step 19. Exemplarily, 1 ml of a 0.2% solution of a dye, preferably methylene blue, may be added. Depending on the desired characteristics of the coupling liquid 18, any suitable compound may be additionally added to the coupling liquid 18.

FIGS. 5a and 5b exemplarily show fixation means to fix a container 10 to an ultrasound device. The fixation means preferably are in the form of an adaptor element 20 having a base member 22 and a lid member 21 which is pivotably coupled to the base member 22. FIG. 5a shows the adaptor member 20 in an open state. The base member 22 is configured such that a container 10 may be inserted between the outer walls of the member. For ease of handling, the adaptor member 20 may further comprise a handle 24. Additionally, the base member 22 comprises at least one fixation means 23 to reversibly secure lid member 21 to base member 22 in a closed state. Such a closed state is shown in FIG. 5b. By pivoting lid member 21 back onto the base member 22, the container 10 is securely connected in the adaptor member 20, preferably through clamping of the border 8 of the container 10 between the lid member 21 and the base member 22. The lid member 21 is secured to the base member 22 by means of fixation means 23. The fixation means 23 may be of any suitable form and configuration, such as screws, pins or a form fit connection. Both the base member 22 and the lid member 21 are configured in such a way as to allow connection means, here shown as tubes 5,6, to be freely connected e.g. to a probe head.

FIG. 6 is a representation of an ultrasound device 25 comprising cooling and/or connection means for the container 10. In this example, the cooling means are provided within the ultrasound device 25. Adaptor member 20 with a container 10 mounted therein is inserted in a receptacle 30 provided on the ultrasound device 25. The cooling means are arranged in such a way as to provide optimal cooling of the container 10 once inserted in the receptacle 30. The ultrasound device 25 preferably further comprises an ultrasound probe head 26, a pivot arm 27 as well as input/output means, such as screen 28. Most preferably, the ultrasound probe head is covered by a cover member 29. In a special embodiment, container 10 and cover member 29 are comprised in a kit. Cover member 29 and the container 10 may then be brought in fluid connection by means of tubes or the like. Further, the ultrasound device may comprise at least one pump to allow cycling of the coupling liquid between the container 10 and the cover member 29.

The invention claimed is:

1. An ultrasound coupling liquid comprising:
   a liquid aqueous solution of at least one hydrophilic polymer, wherein the hydrophilic polymer is or comprises polyvinylpyrrolidone having an average molecular mass of between 30,000 and 70,000; and
   at least one alcohol with a carbon chain of 1 to 7 carbon atoms for reducing reflection of ultrasound waves at the boundary between the coupling liquid and at least one of skin and a cover member covering an ultrasound transducer, wherein
   the at least one alcohol is present in a concentration of 5% to 20% by weight, and the coupling liquid has a viscosity between $1 \cdot 10^{-4}$ Pa·s and $2 \cdot 10^{-4}$ Pa·s at 20° C.

2. The ultrasound coupling liquid as claimed in claim 1, wherein the at least one alcohol is selected from a group consisting of ethanol, propanol isopropanol, benzyl alcohol.

\* \* \* \* \*